United States Patent [19]
Miyagi et al.

[11] Patent Number: 6,104,853
[45] Date of Patent: Aug. 15, 2000

[54] DETACHABLE LASER PROBE HAVING REDUCED ATTENUATION

[75] Inventors: Mitsunobu Miyagi, Miyagi; Akihito Hongo, Ibaraki; Yoshihide Okagami, Kyoto, all of Japan

[73] Assignee: Hitachi Cable, Ltd., Tokyo, Japan

[21] Appl. No.: 09/019,696

[22] Filed: Feb. 6, 1998

[30] Foreign Application Priority Data

Feb. 7, 1997 [JP] Japan ..................... 9-025013

[51] Int. Cl.$^7$ ........................................ G02B 6/02
[52] U.S. Cl. ........................................ 385/125
[58] Field of Search ........................... 385/124–127, 385/141, 147

[56] References Cited

U.S. PATENT DOCUMENTS

| 5,276,761 | 1/1994 | Shimoyama et al. | 385/125 |
| 5,325,458 | 6/1994 | Clifford et al. | 385/125 |
| 5,497,440 | 3/1996 | Croitoru et al. | 385/125 |
| 5,497,441 | 3/1996 | Croitoru et al. | 385/125 |
| 5,729,646 | 3/1998 | Miyagi et al. | 385/141 |

*Primary Examiner*—Akm E. Ullah
*Attorney, Agent, or Firm*—McDermott, Will & Emery

[57] ABSTRACT

A medical laser probe having a dielectric thin film which is coated on the inside wall of a metal pipe and is transparent at a wavelength band of a transmitted laser light is disclosed. The laser probe is detachable to be disposed and reused and satisfies the required characteristics such as low loss transmission, non-toxicity, mechanical strength, heat resistance, moisture resistance, resistance to chemicals, echonomical efficiency, easy-to-use, and the like.

16 Claims, 4 Drawing Sheets

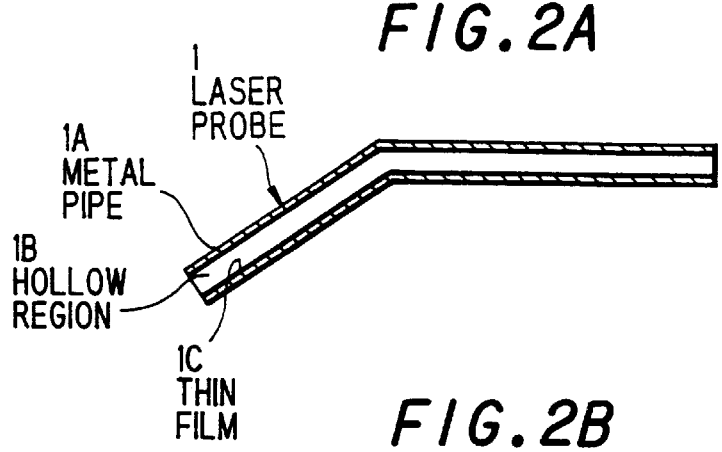
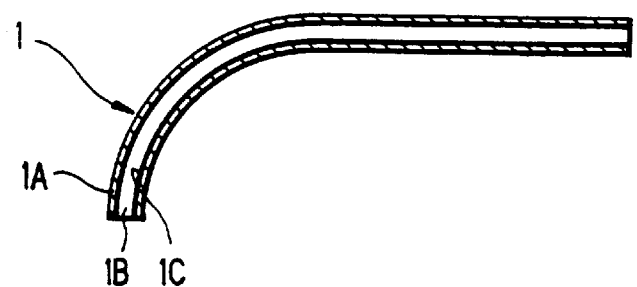
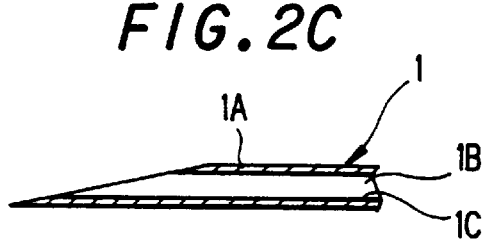
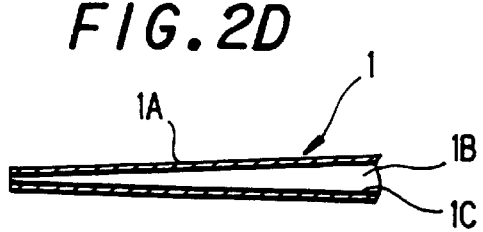
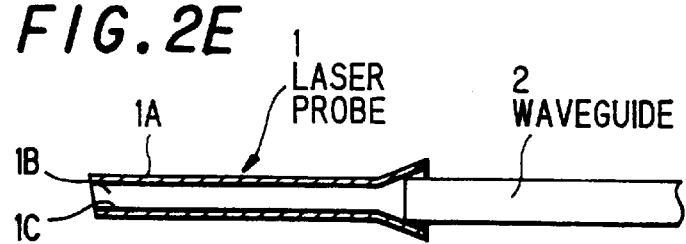

DETACHABLE LASER PROBE HAVING REDUCED ATTENUATION

FIELD OF THE INVENTION

The present invention relates to a laser probe which is disposed to be detachable for disposable or reuse at the leading end of a long waveguide to transmit a laser light or beam of infrared wavelength range used in the medical service field including the dental service, and particularly, to a low loss laser probe at the leading end of which the laser light has a small amount of attenuation.

BACKGROUND OF THE INVENTION

The infrared radiation having wavelengths greater than 2 $\mu$m has been utilized in a variety of fields such as medical service, industrial working, measurement, analysis or chemistry and the like. In particular, Er-YAG laser having a 2.94 $\mu$m wavelength band, CO laser of 5 $\mu$m band, and $CO_2$ laser of 10.6 $\mu$m band have a high oscillation efficiency, a high output, and a high absorption coefficient of water and thus, they are noted as the radiation source of a laser treating device for medical or dental service.

Now, a silica optical fiber which is used for general communication is unsuitable to be used for a waveguide for long distance transmission, because the infrared absorption caused by molecular oscillation becomes large, when a laser light having a wavelength of more than 2 $\mu$m is used therein. Accordingly, the transmission system composed of a material other than the silica optical fiber or various transmission systems having other designs have been proposed and have come in practice.

For example, in the Er-YAG laser for dental treatment being remarked at present, a fluoride glass fiber is used to guide laser light from the light source to the diseased part. The laser light having a wavelength of 2.94 $\mu$m in the Er-YAG laser has the highest absorptance to water among the lasers oscillating in the infrared wavelength range. This laser does not be accompanied with heat or vibration as generated in cutting with an air turbine or electric motor, so that the patient does not feel a pain even under non-anesthesia. Therefore, this laser is capable of cutting the hard tissues like formation of cavities in treatment of carious teeth or removal of dental calculus.

In addition to the cutting of teeth, the medical treatment by the laser has a variety of effects such as incision of soft tissue, arrest of bleeding, sterilization, and the like and laser sources are used in accordance with the respective treating objects. The fluoride glass-fiber has a low loss at the wavelength range of the Er-YAG laser, but it has an increased loss at the wavelength range longer than that range, and thus a chalcogenide glass fiber has been examined for transmission of a CO laser beam. Further, the transmission through the glass fiber is difficult for a $CO_2$ laser beam having further longer wavelength, so that a silver halide or thallium halide crystalline fiber is used therefor. In addition to the solid type of optical fibers, a hollow waveguide, particularly a metal hollow waveguide having a dielectric layer coated on the inside wall thereof and having the desired material and thickness for a particular wavelength of a laser beam to be transmitted has been proposed and examined.

The waveguide to transmit the laser light from the light source to the diseased part is housed within a complicated cable having the long tubes to pass water and gas and the like, and thus, it is technically and economically difficult to dispose the whole of this transmission system or to sterilize it for reuse for each medical treatment. Therefore, it is general means to connect a relatively short and exchangeable laser probe which is utilized for access to, contacting with or insertion into the diseased part, to the leading end of a long waveguide. Since this laser probe is directly exposed to the diseased part or the atmosphere of sterilization, it is required to have various characteristics such as low loss transmission, mechanical strength, heat resistance, resistance to water or chemicals, non-toxicity, easy-to-use, and the like. In order to reuse the laser probe at least, it must withstand the treatments such as sterilization by a high temperature vapor treatment or dipping into chemicals sterilization.

The laser probe is short, but it is one of waveguides to transmit a laser light, and thus, it is conceivable to employ the same material and structure as those of the long waveguide for transmitting the laser light from the light source to the diseased part to make the laser probe. However, the materials to be used for making the above mentioned solid type of infrared transmission optical fibers, that is, the fluoride glass, chalcogenide glass, silver halide or thallium halide crystals can not sufficiently satisfy the performances required for the laser probes described above.

That is, first, the waveguides composed of these materials have generally a low mechanical strength. Although it is capable of using the waveguide by inserting it into a tough metal pipe and the like, the deterioration in the characteristics may occur due to chemical factors in addition to the physical fracture caused by the external force. For example, the fluoride glass will be deliquescent upon exposure to the atmosphere of a high humidity and may break with a progress of crystallization. The silver halide crystals may not only be sensitized by short wavelength light resulting in an increased loss, but also may be chemically reacted upon contact with metals such as iron, copper, aluminium and the like, thereby resulting in degraded optical characteristics and mechanical strength. When the thallium crystal has been held for long periods in a bent state, it slips on the crystal plane resulting in the increase of ductile fracture and scattering loss. Further, these materials are chemically weak as well as mechanically and thus, they can not sufficiently withstand the treatments such as sterilization by a high temperature vapor treatment or dipping into chemicals.

Also, in order to use the laser probe for medical service, it is an essential condition that it is innocuous. The chalcogenide glass or thallium halide crystals contains toxic substances such as As, Se, Tl, etc. These materials have a high refractive index and a relatively low melting point, so that they are subject to the thermal fracture and transpiration in the emitting end of a laser light. Since not only broken slices or pieces but also transpirated vapor are toxic, when these substances invade into the human body, they seriously affect the human body.

From the reasons described above, the laser probes which are made of the materials such as fluoride glass, chalcogenide glass, silver halide or thallium halide crystal and the like, and which are directly contacted with or inserted into the human body can not be used for the medical lasers which have been developed hitherto.

On the other hand, the hollow waveguide has a harmless structure and a high mechanical strength, and is stable to the external atmosphere. However, the hollow waveguide has a problem that dust and/or moisture which deteriorate optical characteristics is liable to invade into the inside thereof. Therefore, it can not be used as such and thus, it is required to prevent the invasion of dust or moisture into the inside of the waveguide.

In the conventional Er-YAG laser for dental treatment described above, a dry air flow in the inside of the tube having a fluoride glass fiber therein is continued during transmitting a laser beam so as to prevent the degradation in mechanical strength of the glass fiber caused by moisture. This laser apparatus has the structure in such a way that it is intercepted from the external atmosphere so that the leading end is directly exposed to the exterior after irradiation by laser light. To the leading end of the glass fiber is connected a short silica glass fiber of 2–3 cm long as a laser probe through a ball lens. This silica glass laser probe is directly contacted with the diseased part and is exposed to the atmosphere such as sterilizing atmosphere and the like for reuse of the laser probe. The silica glass is much superior to the fluoride glass in reliability of the mechanical properties and heat resistance and can sufficiently withstand the inferior environment. However, the silica glass has a sharply increased loss at the wavelength range longer than 2 $\mu$m, and thus, the laser light is attenuated to be a level of approximately 60% even through the laser probe having only a 2–3 cm long. This drop in transmission efficiency imposes new burdens such as improvements in a transmittance of a long waveguide or in an output capacity of a light source and the like on the laser apparatus. Further, there are cases where a laser probe having a length greater than 10 cm is required or the laser probe must be formed with a particular shape such as bent, curved shapes, etc. depending upon a particular object of medical treatment. The silica glass can not sufficiently meet these requirements in the respects of its loss or workability. Further, a short silica glass laser probe can barely be used for the wavelength of the Er-YAG laser, but even such a short silica laser probe can not be used for the CO laser or $CO_2$ laser which oscillates at a longer wavelength As described above, in the medical lasers which are now developing, the laser probes which are high in reliability, low in attenuation of a laser light, and safe and easy in use have hardly come in practice. They can not make full use of the inherent features of the laser treatment, and the effective cases applied to the laser treatment are very limited.

SUMMARY OF THE INVENTION

Accordingly, it is an object of the invention to provide a laser probe in which the transmission loss is largely reduced.

It is another object of the present invention to provide a laser probe for medical service which is detachable for disposable or reuse and satisfies the required characteristics such as mechanical strength, heat resistance, moisture resistance, resistance to chemicals, non-toxicity, optical transmission efficiency, economical efficiency, easy-to-use, and the like.

According to the first feature of the present invention, a laser probe includes a metal pipe; and a dielectric film which is coated on the inside wall of the metal pipe, the dielectric film being transparent at a wavelength range of a laser light to be transmitted.

According to the second feature of the present invention, a laser probe includes a waveguide to transmit a laser light; a metal pipe having a dielectric thin film which is transparent at a wavelength band of the laser light to be transmitted, the dielectric thin film being coated on the inside wall of the metal pipe; and means for connecting the metal pipe to the leading end of the waveguide.

In the laser probes described above, the metal pipe may be formed in the shape of a straight, bent or curved pipe, it may be obliquely cut in the laser light emitting end thereof, it may be formed to have the enlarged and flared shape on the waveguide connecting side, or it may be tapered toward the laser emitting end. Preferably, the metal pipe may be formed by stainless steel or phosphor bronze, and has a roughness less than 1 $\mu$m on the inside surface thereof. Also, the metal pipe may have a metal thin film which is different in material from the metal pipe to be formed on the inside wall thereof and a dielectric thin film formed on the metal thin film. This metal thin film may be formed by silver- or gold-plating onto the inside wall of the metal pipe. Preferably, the dielectric thin film is formed by flowing a solution of a dielectric material or its precursor into the metal pipe to be then heat-treated, dried and cured. The dielectric material may be of polyimide, fluororesin, polysiloxane, polysilazane, cyclopolyolefin, metal oxide or metal sulfide. Preferably, at least one gas selected from the group consisting of air, oxygen, nitrogen, and carbon dioxide gases is passed through the inside of the metal pipe in the direction of laser light emitting end to emit at least one gas from the laser light emitting end to a diseased part of a patient.

The laser light emitting end of the metal pipe may be sealed by a sealing chip which is flat plate-shaped or conically point-shaped or obliquely cut in section, and which has a window or lens function. The connection means may connect the long waveguide with the metal pipe through the flat window or lens which is transparent at the wavelength range of the laser light. The sealing chip may be formed by silicon, diamond, sapphire, silica, magnesium oxide, or calcium fluoride. The long waveguide may be composed of a solid type waveguide transmitting the laser light and a guard member disposed on the outside of the waveguide whereby a dry gas passed through the space between the waveguide and the guard member is supplied to be passed through the inside of the metal pipe of the probe or the gap formed by the metal pipe and a separate metal pipe disposed on the outside of the metal pipe to spout the dry gas simultaneously with the laser light emission. Furthermore, the long waveguide may be composed of a hollow type waveguide transmitting the laser light whereby the dry gas passed through the inside of the waveguide is supplied to be passed through the inside of the metal pipe or the gap formed by the metal pipe and a separate metal pipe disposed on the outside of the metal pipe to spout the dry gas simultaneously with the laser light emission.

Double or more sheathing members may be disposed over the metal pipe radially with predetermined gaps, and a mixed fluid of air, oxygen, nitrogen or carbon dioxide and water may be spouted from the predetermined gaps to the vicinity of the laser light emitting part simultaneously with said laser light emission; or double or more sheathing members may be disposed over the metal pipe radially with predetermined gaps, and an air, oxygen, nitrogen or carbon dioxide gas is spouted from one of the predetermined gaps, while water is spouted from the other predetermined gap, respectively, to the vicinity of the laser light emitting part simultaneously with the laser light emission.

Further, a laser probe may be used by applying plastic deformation to the metal pipe to be bent according to the object of the use of such a laser probe.

Owing to the constructions described above, the laser probe of the present invention can satisfy various required characteristics such as low loss transmission, non-toxicity, mechanical strength, heat resistance, moisture resistance, resistance to chemicals, economical efficiency, easy-to-use, and the like, as a medical service laser probe exposed to the severe environment such as surgical treatment or sterilization for its reuse. In addition, it has advantages in that the inside of the laser probe is not contaminated by dust, soil, etc. That is, the laser probe of the present invention has strength and resistance to occurrence of physical fracture caused by an external force and the like or deterioration of properties caused by chemical change. Also, the laser probe can satisfy the innoxious requirement which is essential for medical treatment, and it can be directly in contact with or be inserted into the human body.

Further, the laser probe may be formed with suitable shapes depending upon the place and object for treatment, and it may be provided with a sealing chip having one of various shapes to be bonded thereto, so that it can comply with various handlings such as its insertion into a very narrow cavity, its insertion into the human body like an injection needle, or its use for a mechanical incision like a scalpel. Consequently, the laser probe can sufficiently make use of the original features thereof for the laser treatment such as cutting, incision, stanching, sterilization and the like and thus, it can be applied to even the cases to which it has not been applied so far.

In addition, the laser probe satisfactorily provides a low loss transmission as a waveguide, so that it can transmit a laser light with a high efficiency, and it does not increase a burden such as the increase in capacity of a laser light source and the like. Further, it can be easily made using inexpensive materials, so that it can be not only reused through sterilization, but also disposed at each treatment.

These and other objects, features, and advantages of the present invention may be more clearly understood and appreciated from a review of the following detailed description of the disclosed embodiments and by reference to the appended drawings and claims.

BRIEF DESCRIPTION OF THE DRAWINGS

FIG. 2A is a sectional view of a bent type of the laser probe of the present invention, FIG. 2B is a sectional view of a curved type of the laser probe of the present invention, FIG. 2C is a sectional view of the laser probe having a obliquely cut leading edge according to the present invention, FIG. 2D is a sectional view of the laser probe having a tapered leading edge according to the present invention, FIG. 2E is a sectional view of the laser probe having a flared connecting part according to the present invention, wherein a waveguide which may be solid or hollow is not shown in a sectional view, but in a frount view.

DESCRIPTION OF THE PREFERRED EMBODIMENTS

Figure 1A:
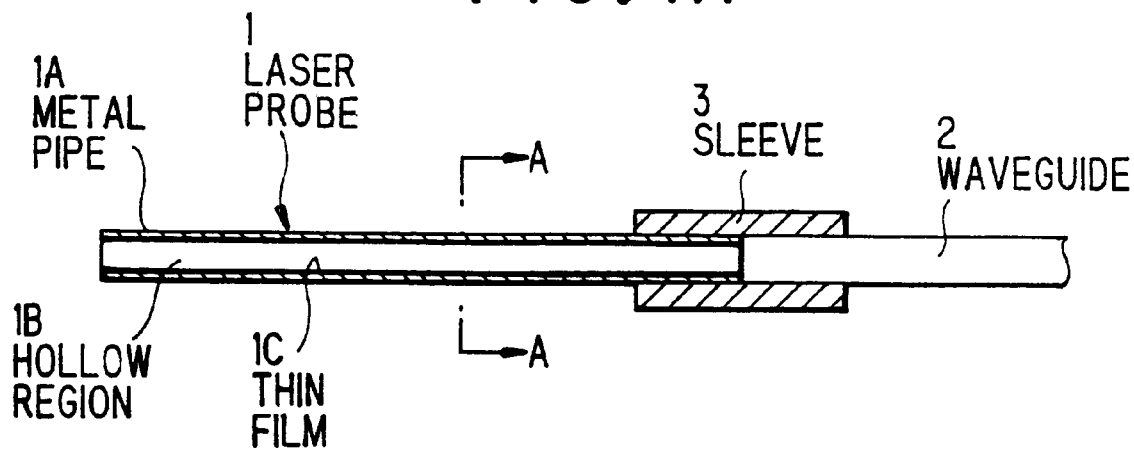
FIG. 1A is a sectional view of the laser probe of the present invention, wherein a waveguide which may be solid or hollow is not shown in a sectional view, but in a frount view.

Referring now to the drawings, in which like numerals indicate like elements throughout the several views, FIG. 1A shows a first preferred embodiment of a laser prove according to the present invention in cross-section. The preferred embodiment includes a laser probe 1 consisting of a hollow metal pipe, a long waveguide 2 for transmitting a laser light from a laser light source (not shown) to a diseased part of a patient and a sleeve 3 for butting the laser probe 1 to the long waveguide 2.

Figure 1B:
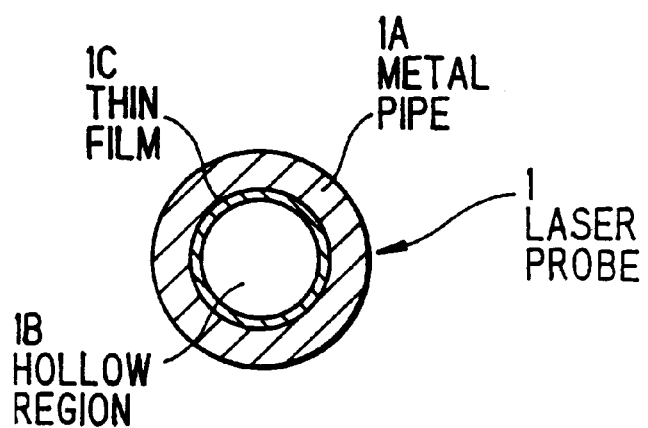
FIG. 1B is a cross-sectional view of the laser probe taken as indicated by the line A—A on FIG. 1.

FIG. 1B shows a sectional view taken on a line A—A of FIG. 1A. The laser probe 1 has a dielectric thin film 1C on the inner wall of the metal pipe 1A, and the thin film 1C is transparent at a wavelength of the laser light transmitted within the hollow region 1B. The laser light is led to an emitted end of the laser probe 1 by repeating the reflections at the interface between the hollow region 1B and the dielectric thin film 1C, and the interface between the metal pipe 1A and the dielectric thin film 1C.

FIGS. 2A–2E show examples of the laser probes 1. In laser treatment, an appropriate one of the laser probes 1 is selected for use corresponding to the position to irradiate a laser light or the object of the laser treatment. For example, in a laser apparatus for dental treatment, it is preferred to use a straight tubed laser probe 1 in the case where the laser light is irradiated on the surface of teeth or the gingiva or gum, and it is preferred to use a bent type laser probe 1 as shown in FIG. 2A or a curved type laser probe 1 as shown in FIG. 2B in the case where the laser light is irradiated on the backside of the teeth. Such a bent or curved laser probe 1 may be preformed, but it is not limited to this preformation, and thus it is possible to apply an arbitrary plastic deformation thereto by users, for example, doctors and others for shape-correction of the laser probe 1 in accordance with the object of using it.

Preferably, the laser probe 1 having a leading edge obliquely cut like an injection needle as shown in FIG. 2C is used in the case where it is inserted into a soft tissue such as the gingiva and the like or for incision. The laser probe 1 has a fine diameter such as the inside diameter ranging from about 200 to about 800 $\mu$m and the outside diameter ranging from about 400 to about 1000 $\mu$m, and for insertion into a narrow cavity, it is preferably to use a laser probe 1 having a gradually tapered leading edge as shown in FIG. 2D.

For the long waveguide 2 is used a hollow waveguide having the structure similar to that of the laser probe 1 according to the present invention, or a solid type optical fiber such as a fluoride glass fiber and the like. When the laser probe 1 has approximately the same diameter as that of the long waveguide 2, they can easily be butt-jointed by the sleeve 3. Furthermore, the laser probe 1 having a flared connection is effective for the easy alignment of optical axes and the easy installation and removal thereof to result in a lower connection loss when the laser probe 1 has a diameter smaller than that of the long waveguide 2, that is, in the connection of two different diameter waveguides.

The attenuation of a laser light in the laser probe 1 varies with the surface roughness of the inside wall of the waveguide 2 and its material. The laser probe 1 of the present invention has the surface roughness less than 1 $\mu$m in the inside wall by polishing the inside wall of the metal pipe 1A. In the laser probe 1 used in the infrared region, the laser light for the laser probe 1 made of the metal such as silver or gold being in contact with the dielectric thin film 1C has a less attenuation value than that of the metal such as stainless steel or bronze. However, the metal pipe 1A made of silver or gold has an insufficient mechanical strength and is very expensive and thus it is not practical from economic consideration. Therefore, the metal pipe 1A in the present invention consists of a stainless steel or phosphor bronze pipe and a metal thin film of silver or gold plated on the inside wall of the pipe 1A. Such a silver or gold thin film can easily be formed by allowing an electroless plating solution to flow into the inside wall of the stainless steel or phosphor bronze pipe.

On the other hand, the attenuation of the laser light transmitted within the laser probe 1 is also remarkably affected by the dielectric thin film 1C. The material of the dielectric thin film 1C is required to be transparent for the transmitted laser light and its thickness must be suitably selected depending upon the wavelength of the laser light. Among particular materials having liquid precursors such as polymer resin, there are some materials having a high transmittance in the infrared region, so that a thin film having a uniform thickness can be easily coated on the inside wall of a fine pipe by flowing the liquid precursor into the pipe, drying and curing it by heat treatment.

The polymer resin such as polyimide, fluororesin, polysiloxane, polysilazane, cyclopolyolefin, and the like can be used as the above coating material. In particular, polyimide is excellent in heat resistance and is transparent even at the long wavelength range of CO laser or $CO_2$ laser and thus it also can be used for a high energy laser probe. Further, in addition to the above organic polymer resin, an inorganic metal oxide or metal sulfide such as ZnO or ZnS and the like, may be used.

The laser probe 1 of the present invention has a hollow structure, so that the cut pieces and scattering liquid generated upon irradiation of a laser beam onto the diseased part have the potential to adhere to the inside wall of the probe 1 resulting in contamination of the inside wall. In order to prevent such a contamination, it is effective to make an inflow of a high pressure gas into the laser probe 1 in the transmitting direction of the laser light and an emission of the gas flow from the leading edge of the probe 1. The high pressure gas such as air, oxygen, nitrogen or carbonic acid gas may be used.

Figure 3A:
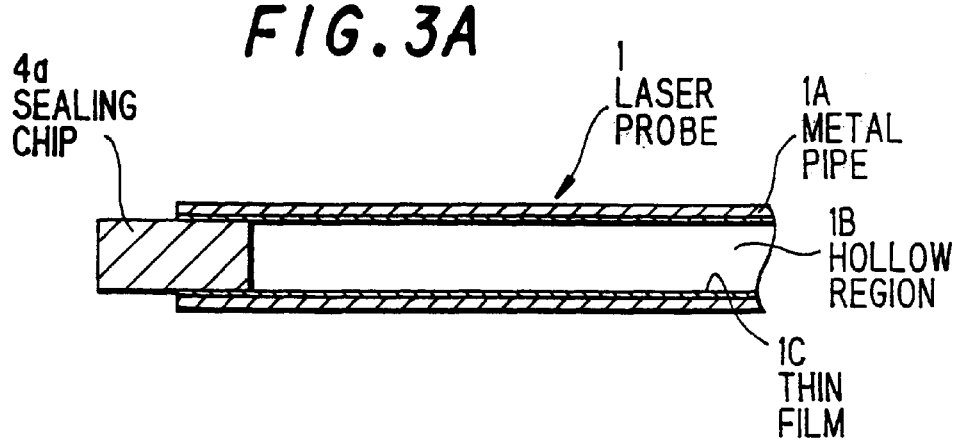
FIG. 3A is a sectional view of the laser probe having a flat sealing chip according to the present invention.
Figure 3B:
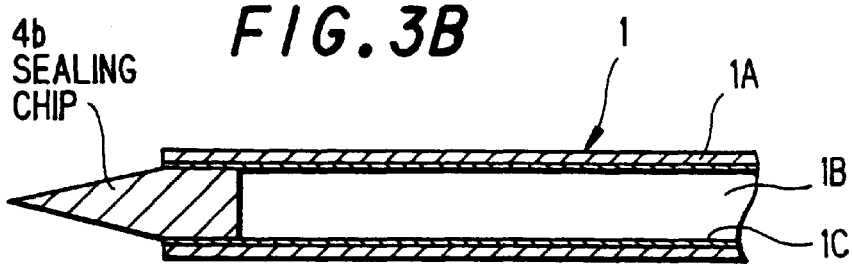
FIG. 3B is a sectional view of the laser probe having a sealing chip with a conical leading edge according to the present invention.
Figure 3C:
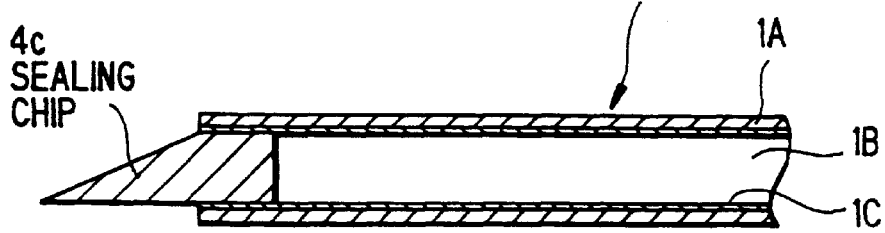
FIG. 3C is a sectional view of the laser probe having a sealing chip with an obliquely cut leading edge according to the present invention.
Figure 3D:
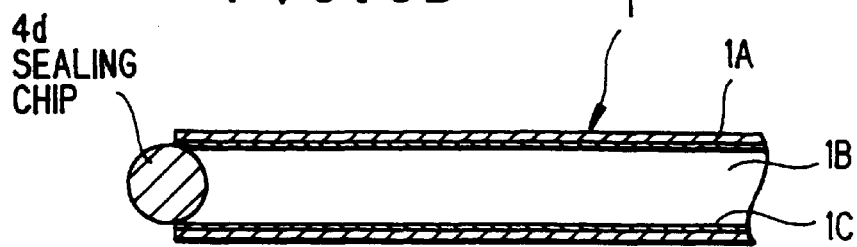
FIG. 3D is a sectional view of the laser probe having a balllens-shaped sealing chip according to the present invention.

FIGS. 3A–3D show laser probes 1 having different constructions. They have window and/or lens functions and are provided with sealing chips 4a, 4b, 4c and 4d to seal the leading end of the laser probes 1, respectively. One of the sealing chips 4a, 4b, 4c and 4d is suitably selected depending upon the objects of treatment or the positions irradiated by the laser light, respectively. For example, the cylindrical chip 4a as shown in FIG. 3A is used for uniformly irradiating a laser light to a diseased part, and a sealing chip having a conically point-shaped tip 4b as shown in FIG. 3B is used for the treatment of a narrow part, because a laser light is converged at the tip point thereof, while a sealing chip having an obliquely cut tip 4c as shown in FIG. 3C is used in the incision of soft tissues. The sealing chip 4b can also be used in irradiation of a laser light into the very narrow cavity, and the sealing chip 4c can also be used in irradiation of a laser light to the back side of teeth because the laser light is reflected from the oblique plane to irradiate the back side of teeth laterally. A ball lens-shaped sealing chip 4d as shown in FIG. 3D is used in a case of making the laser probe 1 contact with the diseased part for cutting or incision thereof. The laser probe 1 having the ball lens-shaped sealing chip 4d indicates a far increase in power density of a laser light at the leading edge of the probe 1. However, with increase in the distance of the probe leading edge from the diseased part, the laser light is more diffused resulting in a rapid decrease of the power density, thereby providing a high security.

The material of the sealing chips 4a, 4b, 4c and 4d is selected depending upon the treating object or the wavelength of a laser light. The material such as silicon, quartz, diamond, sapphire, magnesium oxide, or calcium fluoride is used for the Er-YAG laser, the material such as silicon, sapphire, magnesium oxide, or calcium fluoride is used for the CO laser, and the material such as silicon, diamond or calcium fluoride can be used for the $CO_2$ laser. The sealing chips have a diameter ranging from about 200 to about 800 $\mu$m and a length of less than several millimeters, and thus even if the material has a somewhat larger absorption coefficient, it can inhibit the attenuation of laser light, and it is fine and thus it does not give a large economical burden on the laser probe even if an expensive material such as diamond is used.

The connection of the laser probe 1 with the long waveguide 2 is effected by butting their both ends within the sleeve 3 when both ends have approximately the same diameter. In particular, when the long waveguide 2 is hollow, the contamination of the probe inside wall can be prevented by permitting a high pressure gas to flow into the long waveguide 2 and to emit the high pressure gas from the leading end of the laser probe 1. Further, in order to protect the long waveguide end for emitting the laser light from the external atmosphere when the laser probe 1 is removed from the long waveguide 2, or in order to inhibit the attenuation of a laser light caused by the connection of the laser probe 1 with the long waveguide 2, it is preferable to intervene a flat plate-shaped window or lens between them.

Figure 4A:
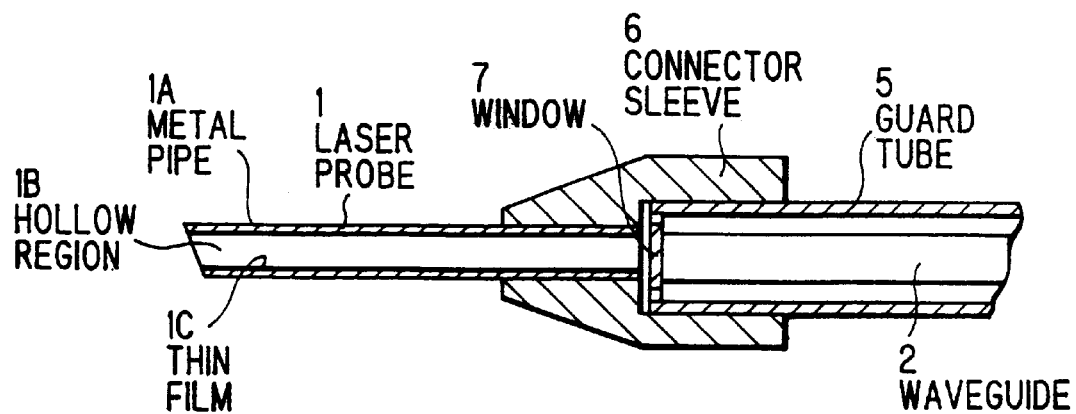
FIG. 4A is a first sectional view of a portion for connecting the laser probe to a long waveguide according to the present invention, wherein a waveguide which may be solid or hollow is not shown in a sectional view, but in a frount view.
Figure 4B:
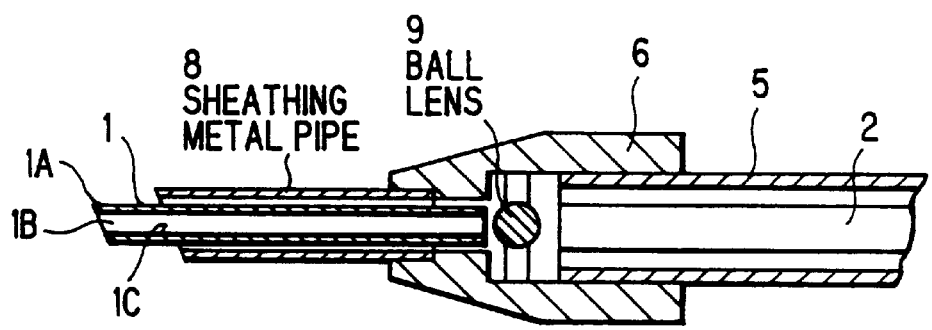
FIG. 4B is a second view of a portion for connecting the laser probe to a long waveguide according to the present invention, wherein a waveguide which may be solid or hollow is not shown in a sectional view, but in a frount view.
Figure 4C:
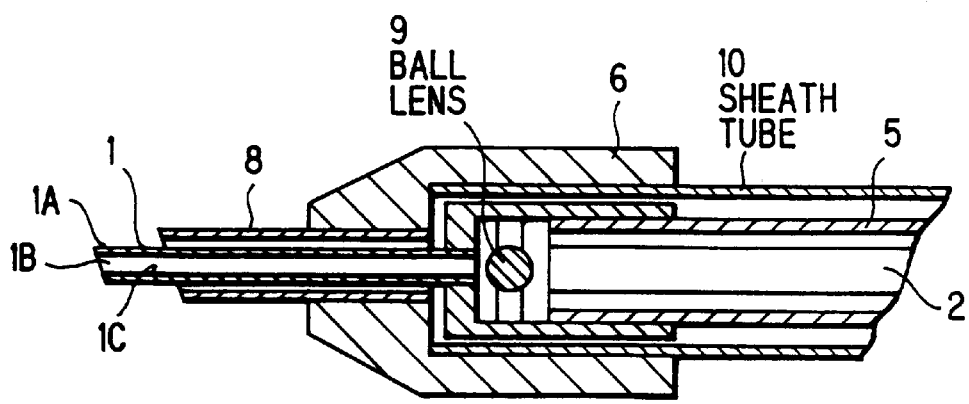
FIG. 4C is a third sectional view of a portion for connecting the laser probe to a long waveguide according to the present invention, wherein a waveguide which may be solid or hollow is not shown in a sectional view, but in a frount view.

FIGS. 4A–4C show a connection portion of the laser probe 1 with the long waveguide 2, respectively. FIG. 4A shows a first preferred embodiment of the connection portion, in which the long waveguide 2 is accommodated in a metal or resin guard tube 5, and a flat plate-shaped window 7 is held at the emitting end of the long waveguide 2 by a holding member which is not specifically explained herein, wherein the holding member has a passage to flow a gas from the side of the long waveguide 2 to the side of the laser probe 1. When the long waveguide 2 is an optical fiber made of the fluoride glass disliking the moist air, and the like, it is effective for prevention of the deterioration in mechanical properties of the long waveguide 2 caused by its chemical reaction to permit a dried gas to flow into the space between the long waveguide 2 and the guard tube 5.

In addition, the window 7 has a function to guard the emitting end of the long waveguide 2 when the laser probe has been removed. That is, the direct soiling or harming, and chemical deterioration of the end surface of the long waveguide 2 can be prevented by the window 7. Further when the long waveguide 2 is hollow, the ingress of dust or moisture from outside is prevented by the window 7. The gas flowed into the space between the long waveguide 2 and the guard tube 5 can detour the window 7 through the passage of the holding member to flow into the laser probe 1. The long waveguide 2 and the laser probe 1 are connected each other with a detachable connector sleeve 6. As shown in FIG. 4A, this connector sleeve 6 is formed by a separate member from the laser probe 1, but both members can simply be unified by using a metal pipe such as the flared laser probe 1 as shown in FIG. 2E.

The first connection portion shown in FIG. 4A is effective when the laser probe 1 has a diameter approximately equal to or larger than that of the long waveguide 2. When the laser probe 1 has a diameter less than that of the long waveguide 2, or when a certain amount of gap between the laser probe 1 and the long waveguide 2 is required, we can use a lens instead of a window, so that an optical loss in connection of them can be reduced by once focusing the emitted light from the long waveguide 2 and again permitting the focused light incident into the laser probe 1.

FIG. 4B shows a second preferred embodiment of the connection portion in which the laser probe 1 and the long waveguide 2 are connected each other through a ball lens 9 within the connector sleeve 6, wherein the ball lens 9 is held in the connector sleeve 6 by a holding member (not specifically explained herein) which has a passage to flow a gas from the side of the long waveguide 2 to the side of the laser probe 1. On the outside of the laser probe 1 is provided a separate sheathing metal pipe 8 and on the outside of the long waveguide 2 is provided a metal or resin guard tube 5. The light emitted from the long waveguide 2 is focused by the ball lens 9 and then is incident into the laser probe 1. Gas can be flowed into a space or gap between the long waveguide 2 and the guard tube S, or in the case where the long waveguide 2 is hollow, gas can be flowed into the inside of the hollow long waveguide 2. This gas is detoured around the ball lens 9 through the passage of the holding member and is flowed into the laser probe 1 or the gap between the laser probe 1 and its outer sheathing metal pipe 8. In addition to the protection of the long waveguide 2 and the laser probe 1, this gas acts as an assist gas to increase the efficiency of cleaning or incision by spouting around the diseased part onto which a laser beam is emitted.

As shown in FIG. 4B, the laser probe 1 has a double structure, that is, it is protected by the sheathing metal pipe 8. This laser probe 1 can also be made into a triple structure by disposing a separate metal pipe on the outside of the sheathing metal pipe 8. The laser light is transmitted in the inside of the center laser probe 1, gas can flow on the outside thereof and water can flow on the outside of the sheathing metal pipe 8. In this way, the laser light, gas, or water can be supplied by utilizing a separate route or space, respectively, and further, the laser and gas, or gas and water can utilize a common route, respectively.

FIG. 4C shows a third preferred embodiment of the connection portion in which a sheath tube 10 is further provided on the outside of the guard tube 5 disposed on the outside of the long waveguide 2. A fluid such as water or a mixture of water and gas flows through the space between the guard tube 5 and the sheath tube 10 to detour around the ball lens 9 through a passage of a holding member as explained in FIG. 4B, and flows through the space between the laser probe 1 and the sheathing metal pipe 8 to be emitted on the diseased part on the basis of irradiation of a laser light. Gas can be allowed to flow into a gap between the guard tube 5 and the long waveguide 2, or in case that the long waveguide 2 is hollow, gas can be allowed to flow into the inside of the hollow long waveguide 2 and this gas flows through the inside of the laser probe 1 along with a laser light to be emitted from the leading edge thereof.

In general, the mid-infrared laser light is well absorbed by water, so that the laser probe 1 is formed longer than the sheathing metal pipe 8. More concretely, it is preferred to expose the leading end of the laser probe 1 about 5 mm from the end of the sheathing metal pipe 5. In this way, it is effective for dental treatment to irradiate the laser light to the diseased part while injecting air and water to the vicinity thereof.

In the construction of the present invention described above, the inflow gas into or around the laser probe 1 has a variety of functions such as the inhibition of deterioration in mechanical and optical properties due to the isolation from the external atmosphere, prevention of thermal damage of optical members, prevention of the invasion of pollutants such as dust, moisture and the like, removal or cleaning of incised pieces in the diseased part, assist of an incision efficiency, etc., and other various functions depending upon kinds of treatment. In the present invention, one of air, oxygen, nitrogen and carbon dioxide gases was used while taking into consideration of these gas functions. The use of dry gas having the minimum moisture content is especially effective in inhibition of the deterioration in mechanical and optical properties of the long waveguide 2 or laser probe 1. Also, the use of cooled gas is effective for prevention of thermal damage of them.

Further, preferably, the window 7 or the ball lens 9 is formed by any one of the materials such as silicon, diamond, sapphire, silica, magnesium oxide, and calcium fluoride similarly to the sealing chips 4a, 4b 4c and 4d to seal the leading end of the laser probe 1.

When the laser probe 1 according to the present invention is applied to the Er-YAG laser, it was confirmed by the present inventor that the curved type laser probe 1 could provide a 80% of transmittance. This value is about 10 to 20% higher than the value obtained by a silica laser probe of a similar shape. Similarly, it was confirmed that the $CO_2$ laser probe having a length of 10 cm or more to insert it into the body has a sufficient transmittance as well as an easy handling quality.

The laser probes described above have the following effectiveness:

(1) the occurrence of physical fracture caused by an external force and the like or the deterioration of properties caused by chemical change is difficult and they are tough, and thus they have a sufficient durability even in the severe environment such as surgical treatment or bacteria sterilization;

(2) they satisfy the innoxious requirement which is one of the essential requirements for medical treatment;

(3) it is possible to select a laser probe of a suitable shape corresponding to the place and object for treatment, and to fit up the leading end of the laser probe with one of various sealing chips, and thus they can comply with various handlings such as insertion of them into a very narrow cavity, insertion of them into the human body like an injection needle, or a mechanical incision like a scalpel;

(4) they satisfactorily meet a low loss transmission as a waveguide and can transmit a laser light at a high efficiency, and thus they do not increase a burden such as increase in capacity of a laser light source and the like; and (5) they can easily be made using inexpensive materials, so that they can be disposable as well as reusable through sterilization.

As described above, the laser probes according to the present invention have a dielectric thin film transparent at a wavelength range of a laser light to be coated on the inside of a metal pipe and thus, they can satisfy the required characteristics such as low loss transmission, non-toxicity, mechanical strength, heat resistance, moisture resistance, resistance to chemicals, economical efficiency, easy-to-use, and the like, and are removable, disposable or reusable.

The preferred embodiments of the present invention have been disclosed by way of example and it will be understood that other modifications may occur to those skilled in the art without departing from the scope and the spirit of the appended claims.

What is claimed is:

1. A laser probe, including:

a waveguide to transmit a laser light;

a metal pipe of a first shape having a dielectric thin film which is transparent at a wavelength band of said laser light be to transmitted, said dielectric thin film being coated on the inside wall of said metal pipe; and means for connecting said metal pipe to the leading end of said waveguide;

wherein said metal pipe of the first shape connected to the leading end of said waveguide by said connecting means is replaced by a metal pipe of a second shape in accordance with change of a position to irradiate said laser light.

2. A laser probe according to claim 1 wherein the first shape said metal pipe has a shape selected from the group of shapes consisting of straight, bent and curved shapes.

3. A laser probe according to claim 1 wherein said metal pipe has an obliquely cut end to emit a laser light.

4. A laser probe according to claim 1 wherein said metal pipe has a flared end on the side conneted with said waveguide.

5. A laser probe according to claim 1 wherein said metal pipe has a tapered edge in a direction that said laser is emitted.

6. A laser probe according to claim 1 wherein said metal pipe is composed of a material selected from one of stainless steel and phosphor bronze.

7. A laser probe according to claim 1 wherein at least one gas selected from the group consisting of air, oxygen, nitrogen, and carbon dioxide gases is passed through the inside of said metal pipe in the direction of a laser light emitting end thereof, and said at least one gas is emitted from said laser light emitting end to a vicinity of a diseased part.

8. A laser probe according to claim 1 wherein said metal pipe includes a laser light emitting end that is sealed by a sealing chip which is flat plate-shaped, conically point-shaped or obliquely cut in section, said sealing chip having a window or lens function.

9. A laser probe according to claim 1 wherein said connecting means connects the waveguide to said metal pipe through a flat plate-shaped window or lens which is transparent at the wavelength band of the laser light.

10. A laser probe according to claim 8 wherein said sealing chip is formed by a material selected from silicon, diamond, sapphire, silica, magnesium oxide, and calcium fluoride.

11. A laser probe according to claim 9 wherein said flat plate-shaped window or lens is formed by a material selected from silicon, diamond, sapphire, silica, magnesium oxide, and calcium fluoride.

12. A laser probe according to claim 1 wherein said waveguide is a solid type waveguide transmitting said laser light, a guard member is disposed on the outside of said waveguide, and a gas is passed through a space between said waveguide and said guard member, so that said gas is supplied to be passed through the inside of the said metal pipe, or a gap formed by said metal pipe and a separate metal pipe disposed on the outside of said metal pipe to spout said gas in accordance with an emission of said laser light.

13. A laser probe according to claim 1 wherein said waveguide is a hollow type waveguide transmitting said laser light, a gas is passed through the inside of said waveguide, so that said gas is passed through the inside of said metal pipe, or a gap formed by said metal pipe and a separate metal pipe disposed on the outside of said metal pipe to spout said gas in accordance with an emission of said laser light.

14. A laser probe according to claim 1 wherein two or more sheathing members are disposed over said metal pipe radially with predetermined gaps, and a mixed fluid of air, oxygen, nitrogen or carbon dioxide and water is spouted from a common one of said gaps to the vicinity of a laser light emitting part in accordance with an emission of said laser light.

15. A laser probe according to claim 1 wherein two or more sheathing members are disposed over said metal pipe radially with predetermined gaps, and an air, oxygen, nitrogen or carbon dioxide gas is spouted from one of said predetermined gaps, while water is spouted from another gap of said predetermined gaps to a vicinity of said laser light emitting part in accordance with an emission of said laser light.

16. A laser probe according to claim 1 wherein said metal pipe is bent by applying plastic deformation thereto according to the object of the use of said laser probe.

* * * * *